United States Patent [19]
Biencourt et al.

[11] Patent Number: 5,417,107
[45] Date of Patent: May 23, 1995

[54] METHOD AND CAPACITANCE PROBE ARRANGEMENT

[75] Inventors: Michael P. Biencourt, Chino; John A. DeVries, Tustin, both of Calif.

[73] Assignee: Paul-Munroe Engineering, Orange, Calif.

[21] Appl. No.: 124,957

[22] Filed: Sep. 21, 1993

[51] Int. Cl.⁶ ...................... G01N 27/22; G01N 11/00
[52] U.S. Cl. .................................. 73/61.44; 324/664; 324/689
[58] Field of Search ................. 73/61.44; 324/664, 689

[56] References Cited

U.S. PATENT DOCUMENTS

| | | | |
|---|---|---|---|
| 3,253,606 | 5/1966 | Kuntz | 73/61.44 |
| 4,149,958 | 4/1979 | Martin | 204/302 |
| 4,426,293 | 1/1984 | Mason et al. | 210/636 |
| 4,751,842 | 6/1988 | Ekrann et al. | 73/61.44 |
| 4,926,112 | 5/1990 | Fasching | 324/664 |
| 4,971,015 | 11/1990 | Gonze | 73/61.44 |
| 5,067,345 | 11/1991 | Mougne | 73/61.44 |
| 5,249,455 | 10/1993 | Cox | 73/61.44 |
| 5,272,444 | 12/1993 | Cox | 73/61.44 |

FOREIGN PATENT DOCUMENTS

| | | | |
|---|---|---|---|
| 62-12836 | 1/1987 | Japan | 73/61.44 |
| 894525 | 12/1981 | U.S.S.R. | 73/61.44 |
| 9002941 | 3/1990 | WIPO | 73/61.44 |

Primary Examiner—Hezron E. Williams
Assistant Examiner—J. David Wiggins
Attorney, Agent, or Firm—Gilliam, Duncan & Harms

[57] ABSTRACT

An improved method and capacitance probe arrangement for determining the fluid phase fractions of fluids having differing permitivity such as those of gas, oil, and water and oil-water emulsion in a fluid stream flowing from an oil well which includes trapping the primarily liquid in a vertically disposed chamber. The liquid is held therein to permit separation of the phase fractions to the extent possible within a reasonable time. A number of measurements are taken of the capacitance at a plurality of discrete vertically spaced locations within the chamber. These capacitance measurements relate directly to the varying permittivity of the phase fractions of the various liquids contained therein which may be gas, oil, and water and a oil-water emulsion. The measurements are processed by a data processor to provide precise information on such phase fractions and emulsion interfaces. A number of embodiments of the novel probe are disclosed for determining capacitance at spaced locations within the chamber.

The present method overcomes many of the problems that have plagued prior systems including temperature dependance, fouling of the system by oil build up, lengthy delays of emulsion settling, calibration problems, and changing physical properties of the oil and water in the well stream.

12 Claims, 5 Drawing Sheets

METHOD AND CAPACITANCE PROBE ARRANGEMENT

BACKGROUND

The present invention relates to an improvement in the field of testing liquids more particularly, but not by way of limitation, to a novel method and capacitance probe arrangement for determining the phase fractions of a liquid or a mobile solid.

More recently, U.S. Pat. No. 3,911,256 presented an improved apparatus for testing and analyzing a liquid. This patent provided for diverting and isolating a predetermined volummetric portion of the flow of a liquid and then measuring the differential pressure which is used to determine the density of the isolated portion. This portion was then subjected to compression of the gas fraction so that the volume of gas could be mathematically determined. Other measurements were made of the test portion so that the volume of gas and proportions of each liquid in the sample could be determined by mathematical comparative calculations.

U.S. Pat. No. 4,852,395 discloses a three phase fluid flow measuring system for measuring the volummetric fractions of gas, water and oil which included a centrifugal separator for conducting primary separation of gas from the liquid phase. A sample of the resultant fluid stream was conducted to a test chamber where it was subjected to compression of the gas fraction so that the volume of gas could be mathematically determined. The transmissivity of microwave energy through a section of the flowing stream was then measured as a way of determining the volummetric fraction of water and oil in the liquid phase.

It is also known in the art to meter aggregate flow rate and to segregate a test sample of a well stream and to record the temperature, pressure, and weight of such sample and to also determine the aggregate capacitance of the sample. The net oil, gas, and water content are then determined mathematically, after corrections for temperature.

However, all known prior art systems and methods are subject to a number of shortcomings. Some systems will not provide accurate liquid flow data if over a 5% gas fraction exists in the sample or if the fluids do not separate into their fractions by the force of gravity within a short time period. Also, inaccurate data is obtained as the degree of emulsion of different fluids increases or varies.

These problems include temperature dependance. The capacitance readings vary with sample temperature changes, which the computer must attempt to correct. However, results have been inconsistent between different sample chambers and different coatings on the capacitance probe. As the test chamber or test probes are fouled, test readings begin to vary unacceptably with the computer indicating a lower water fraction than really exists. Great difficulties have been experienced in calibrating capacitance probes which require a cumbersome and difficult procedure. Also, recalibration of current systems must be made in the event that the capacitance of the fluids change over time, or with the addition of chemicals into the fluids. However, the biggest problem remains with emulsions that remain after the time permitted for separation of the fractions and the inconsistencies in capacitance readings that result in indicating a much larger content of a fluid than is actually present. Ultimately, the only way the prior art has found to deal reliably with emulsions is to wait for the sample to separate out completely, which time period may take any where from minutes to weeks, if at all.

While the prior patents and prior art commercial probe devices have been successful to a certain extent, it is nonetheless clear that substantial room exists for affecting an advance in the art which overcomes these shortcomings in a practical and efficient manner.

It is a general object of the invention to provide an improved method and capacitance probe arrangement for testing and analyzing a fluid contained in a tank or chamber to determine the volumetric fractions of the fluids having varying permittivity contained in the tank and which overcomes the shortcomings that are found in the methods and apparatus of the known prior art.

Another object of the invention is to provide an improved method and automated system for determining the phase fractions of an oil well stream wherein the gas, water, and oil fractions of a test sample of the well stream are not separated nor need to be separated in the process of analyzing and calculating the new oil content.

Yet another object of the invention is to provide a method and capacitance probe arrangement which may accurately test and analyze test well samples which have gas fractions from 0 to approximately 100% of the total well production volume.

Another object of the invention is to provide an improved method and capacitance probe arrangement for analyzing a contained liquid having oil as a constituent which will reduce or substantially minimize the effects of any accumulated oil coating on the interior of the test chamber.

It is a further object of the invention to provide a method of analyzing a test sample of a production well stream which will provide additional data beyond the phase fractions of gas, oil and water and which will minimize the dependency on entry of accurate data relating to the densities of oil, gas and water, permitivity of oil, water, gas, etc. thereby providing "live" or real time oil and water density data.

Also, it is an object of the improved method to permit analysis and quantification of the degree of oil-water emulsion of the test sample of the well stream and to indicate the separation rate of the oil and gas fractions.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with the specific embodiments shown in the attached drawings. Briefly stated, the present invention contemplates a novel method and capacitance probe arrangement for calculating the volumetric phase fractions of a contained liquid, gas or a mobile solid which may be comprised of liquids having different permittivities such as those of gas, oil, and water and oil-water emulsion in an oil well production fluid stream flowing from an oil well.

In the illustrated embodiments of the novel probe arrangements of the invention, the capacitance of the sample is measured at a number of discrete spaced locations over the height of the sample, with the capacitance being representative of the permitivity of the sample at each location. The measurements taken are then used by a data processor to solve a plurality of mathematical equations and thereby reveal the phase fractions of gas, oil and water and the oil-water emulsion of the test sample. Such measurements permit the volumes of such constituents to be accurately calculated and to clearly reveal the interfaces of such constituents and the oil-water emulsion and the rate of separation.

The foregoing has outlined rather broadly the more pertinent and important features of the present invention in order that the detailed description of the invention that follows may be better understood so that the present contribution to the art may be more fully appreciated. Additional features of the invention will be described hereinafter which form the subject of the claims of the invention. It should be appreciated by those skilled in the art that the conception and the disclosed specific embodiment may be readily utilized as a basis for modifying or designing other structures and methods for carrying out the same purposes of the present invention. It should also be realized by those skilled in the art that such equivalent constructions and methods do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which.

Similar numerals refer to similar parts in the various embodiments.

DETAILED DESCRIPTION OF THE INVENTION

Figure 1:
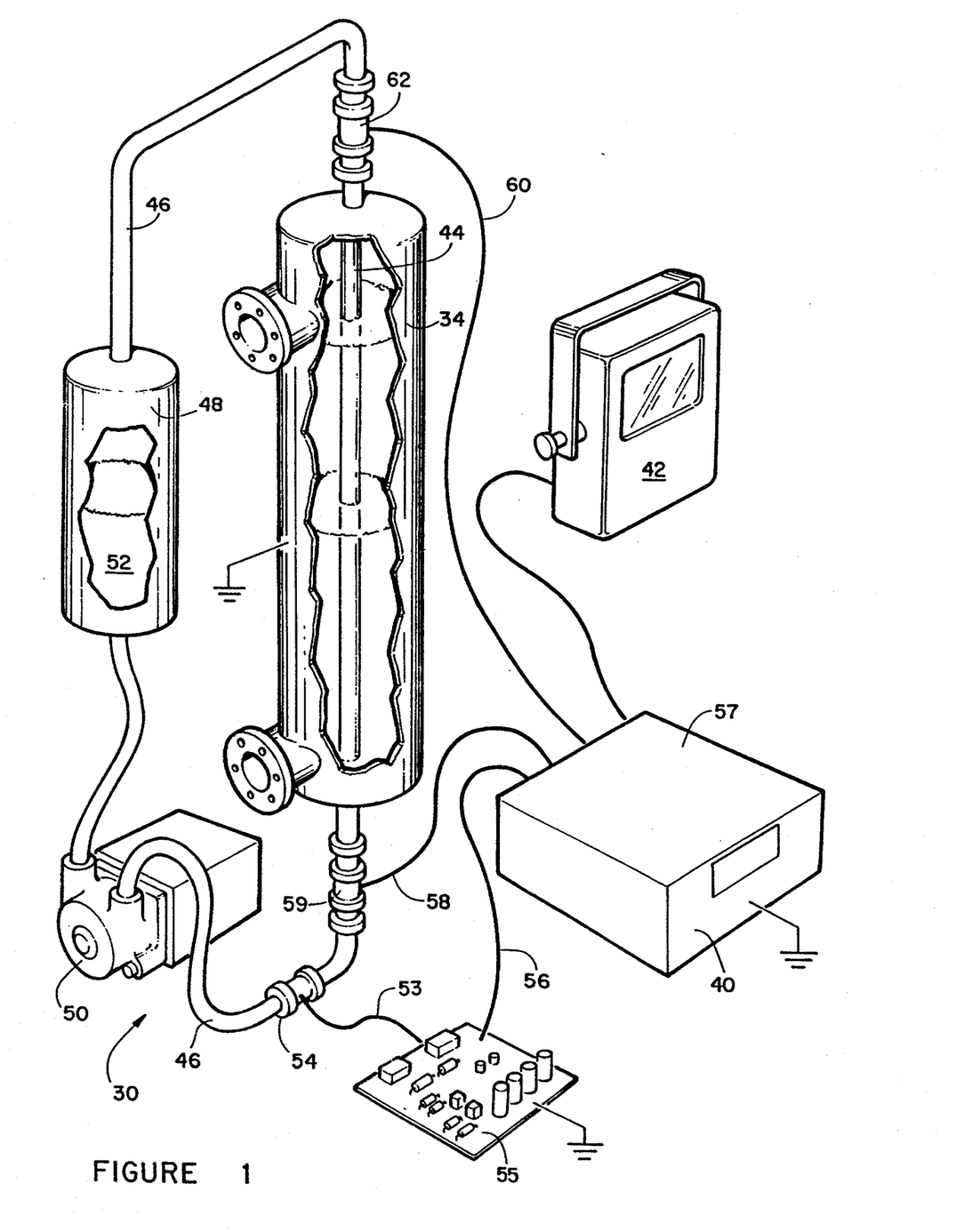
FIG. 1 is a simplified perspective of a presently preferred embodiment of the novel capacitance probe arrangement of the invention.

Referring now to the drawings in detail, and in particular to FIG. 1, the reference character 10 generally designates a novel capacitance probe arrangement constructed in accordance with a preferred embodiment of the invention for carrying out the novel method of the invention.

After an oil well stream to be sampled has been passed through a suitable phase separator or fluid conditioner (not shown) to separate out the majority of gas, the resultant primarily liquid stream is then directed to a vertically disposed sampling chamber 34 which selectively traps a sample of the separated liquid well stream for analysis.

The testing and analysis of the liquid well stream flowing from the phase separator 14 is commenced by permitting the liquid well stream to flow through the sampling chamber 34 to purge the sampling chamber 34 of whatever previous sample of the well stream that had been previously trapped therein for analysis. This step depending on the volume of the liquid stream can be conducted relatively quickly. A sample of the liquid well stream is then trapped within the sampling chamber 34. The sampling chamber 34 has known dimensions with the sample of the separated well steam being trapped therein in a vertical liquid column. A a plurality of measurements are taken of certain aspects of such sample. These measurements, which are taken in a suitable conventional manner, include the absolute temperature, the absolute pressure, and the differential pressure generated by a known liquid column height. In addition, a measurement is taken of capacitance of the sample at a plurality of spaced discrete locations along the vertical height of such sample.

In the preferred embodiment of the invention, the electrical capacitance is measured at each discrete location. The electrical capacitance is indicative of the permittivity of the fluid at such discrete location. These measurements are input to a suitable electrical interface 40 which is coupled to a suitable computer 42 which uses the data obtained to solve for the three unknowns in three equations as will be discussed in greater detail hereinafter. The well data may be displayed in chart form on a full size LCD computer screen (not shown) or displayed graphically by the computer 42 or further operated on in any desired manner.

Referring again to FIG. 1, the novel capacitance probe arrangement for measuring the capacitance over the vertical height of the trapped well stream sample at a number of discrete locations will be discussed in greater detail. As will be seen, in a preferred embodiment of the invention the sampling chamber 34 is provided with a vertically extending hollow tube 44 which extends along the vertical axis of the chamber 34. The tube 44 is electrically nonconductive and is connected at each end to tubing 46 in which is interposed a fluid reservoir 48 and a suitable reversible pump 50. The tube 44 is preferably protected by a suitable sheathing made from a lubricous material such as, for example, Teflon. A suitable electrically conductive fluid 52, such as brine, is contained in the reservoir 48.

A conductor 53 is connected to a suitable conductive coupling 54 that is interposed in the non-conductive tubing 46. The conductor 53 is also connected to suitable capacitance measuring circuitry 55 that is grounded and connected via conductor 56 to a suitable programmable logic controller 57. The programmable logic controller 57 is connected by lead 58 to an electrically conductive coupling 59 interposed in the non-conductive tubing 46 and is also connected by lead 60 to a suitable electrically conductive coupling 62 that is interposed in the non-conductive tubing 46. The conductive coupling 62 is wired to ground through the programmable logic controller 57. The sample container 34 is also grounded. The programmable logic controller 57 is coupled to the computer 42.

After the time period allotted to permit some separation of the phase fractions of the well sample now contained in sample chamber has expired, the pump 50 is actuated to introduce the conductive fluid into the tube 44 at a constant predetermined rate. As the conductive fluid 52 enters and fills the tube 44, the capacitance measuring circuitry 55 measures the changing capacitance whereby the capacitance measurements provide a means for determining the point capacitance along the height of the fluid sample and enable the determination of the permitivity of each phase fraction of the sample.

The capacitance readings provide a capacitance profile that is a very good indication of the phase fractions and indicates precisely the interface between such fractions. Also, and very importantly, the capacitance profile provides a clear indication of both oil-continuous and water-continuous emulsions of the oil-water emulsions since such measurements may be taken at intervals during the separation period.

After the capacitance measurements have been made of the full vertical height of the sampling chamber to provide an indication of the gas, oil and water fractions and the oil-water emulsion of the sample, the pump 50 is reversed to return the fluid 52 to the reservoir 48.

The present invention would also contemplate providing a plurality of electrical capacitance indicators at spaced discrete locations along the interior of tube 44 for providing capacitance readings at each location along the vertical height of the tube 44. Each of the capacitance indicators would be coupled to the capacitance measuring circuitry 55. After the time permitted for some separation of the phase fractions has expired, the pump 50 would then pump the conductive fluid 52 up into the tube as a constant rate. The capacitance readings from the plurality of spaced capacitance indicators could be made simultaneously in parallel or serially as the conductive fluid 52 rises within the tube 44. As soon as the capacitance measurements have been made of the full vertical height of the sampling chamber to provide an indication of the gas, oil and water fractions and the oil-water emulsion of the sample, the pump 50 is reversed to return the fluid 52 to the reservoir 48.

Figure 3A:
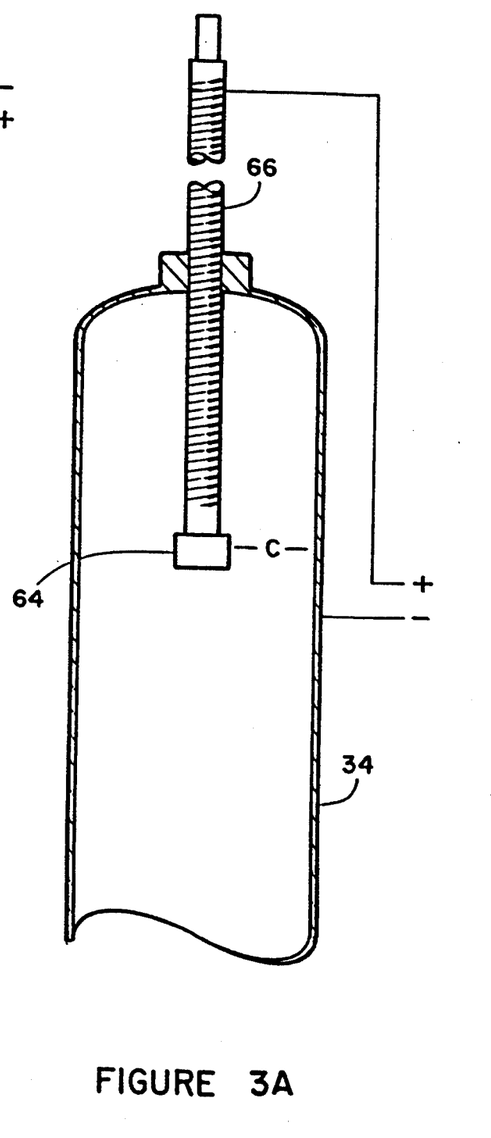
FIG. 3A is a simplified sectional view of another embodiment of the capacitance probe arrangement.
Figure 3B:
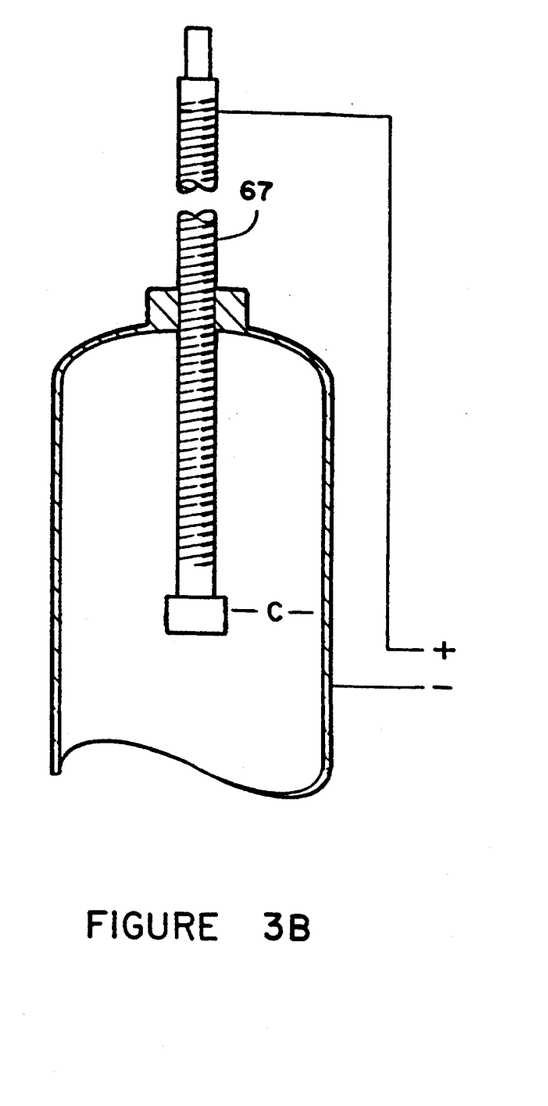
FIG. 3B is a simplified sectional view of still another embodiment of the capacitance probe arrangement.

FIG. 1 illustrated an embodiment of the invention which contemplated moving a conductive column of conductive fluid along the vertical height of the trapped fluid sample in a non-contacting manner and taken a plurality of capacitance measurements along the vertical height of the sample whereby the phase fractions and the oil-water emulsion could be accurately calculated. In FIG. 3 a related embodiment of the invention is illustrated. The embodiment of the invention in this instance contemplates moving an elongate member vertically, either up or down, within the fluid sample trapped in the sample chamber 34 and taking capacitance measurements during such movement. In FIG. 3, a small capacitance indicator 64 which is electrically coupled to the capacitance measuring circuitry 55 is positioned on the end of a suitable electrically non-conductive rod 66 which is reciprocally moved vertically within the fluid sample contained in the sampling chamber 34 as capacitance readings are taken. While FIG. 3 shows an electrically non-conductive rod 66 being utilized to vertically move the capacitance indicator 64 reciprocally within the sample chamber, other means, such as a suitable cable system, would also be within the scope of the invention for moving the capacitance indicator 64 within the chamber 34.

Also, while FIG. 3 shows a capacitance indicator 64 secured to a reciprocal electrically non-conductive member 66 for taking a plurality of capacitance readings along the vertical height of the liquid column of the sample contained in the chamber 34, the capacitance readings along the vertical axis of the sample could also be made by using only an elongate conductive member 66 that is vertically reciprocated in the sample contained in the chamber 34 without providing a capacitance indicator 64. The conductive member 67 in this instance, would be electrically coupled to the capacitance measuring circuitry 55 so that capacitance readings could be taken as the conductive member 67 was reciprocally moved vertically within the fluid sample.

Figure 2:
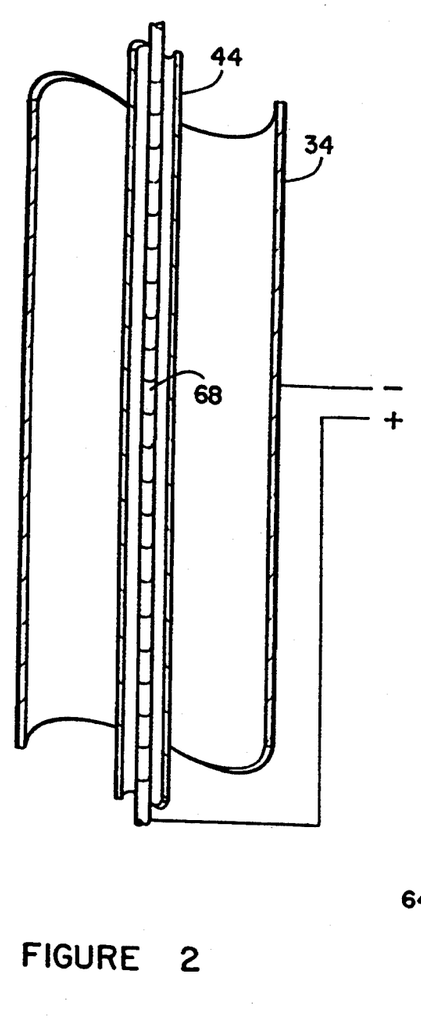
FIG. 2 is a simplified sectional view of another embodiment of the capacitance probe arrangement.

Referring now to FIG. 2, another embodiment of an arrangement for practicing the novel method of measuring the capacitance at a plurality of spaced locations along the vertical height of the liquid sample will be described. In FIG. 2, the sampling chamber 34 is grounded to provide an anode and the central tube is conductive with a non-conductive outer coating such as Teflon. A plurality of spaced capacitance probes 68 are spaced along the interior of the tube 44 at "n" locations. The capacitance probes 68, it will be understood, are suitably coupled to the programmable logic controller 57 and to the computer 42. The measurements of capacitance at discrete locations along the interior of the tube 44 may be made serially or simultaneously when the sample is trapped in the chamber 34 during or after a period of separation or during the filling of the chamber 34. The computations of the phase fractions and the oil-water emulsion are conducted as will be hereinafter described in detail.

The capacitance readings as hereinbefore determined are directly related to the relative permittivity of the gas, oil and water acting as the dielectric constant. As is known, the fractions of gas, oil and water are related to each other by three simultaneous, equations. The three equations are:

$$Fo + Fw + Fg = 1 \tag{1}$$

$$Fo*Rho_o + Fw*Rho_w + Fg*Rho_g = Rho_s \tag{2}$$

$$Fo*Eo + Fw*Ew + FgEg = Es \tag{3}$$

Where:
Fo = Fraction of oil to be found
Fw = Fraction of water to be found
Fg = Fraction of gas to be found
$Rho_o$ = Known density of oil
$Rho_w$ = Known density of water
$Rho_g$ = Known density of gas
Eo = Known permittivity of oil
Ew = Known permittivity of water
Eg = Known permittivity of gas
$Rho_s$ = Measured aggregate density in the sampling chamber
Es = Measured capacitance derived from a plurality of capacitance readings made in the sampling chamber.

Referring now to FIGS. 4 through 9, the invention will be contemplated in perhaps its broadest aspects. For measurement and control activities conducted in various forms Of commerce, capacitance probes are used to measure the permittivity of various liquids.

These probes may be disposed in a vertical position where they can be used to determine the average permittivity of a liquid sample. They may also be used in a horizontal mounting where the signal from the probe can be used to control liquid levels of stratified liquids by furnishing the signal to open or close valves. For example, in an oil field storage tank, it may be necessary or desirable to bleed off incoming free water which may be mixed with a three phase incoming oil, water and gas stream. To control this function, a capacitance probe might be located so as to enter the tank at the desired oil/water interfaces level. When the probe reading indicates that water is at the probe level, the appropriate signal would be sent to the operator or the bleed valve so that it would be opened and the water would be removed from the bottom of the tank. As the water is removed, the oil-water interface would be lowered until the probe capacitance sensing device indicated that oil was now at the probe level. A signal would then be sent to close the valve operator on the bleed valve.

In operations in oil fields, it is often found that there is an emulsion layer located between the free water level at its top and the clean oil level at its bottom most point. At times, both continuous oil phase (water-in-oil) and continuous water phase (oil-in-water) emulsions may be present, and on occasion, they may both be present in the same liquid sample to be tested.

Another use for capacitance probes has been in the field of productions testing of individual oil wells. Typically, oil wells produce a mixture of crude oil, water, oil-water emulsions, natural gases and impurities such as hydrogen sulfide and carbon dioxide in the gases and basic sediment in the liquid stream. The basic sediment may consist of particles of formation rocks such as the sand grains, shale particles and occasionally bits of metallic elements and compounds.

In a previously described type of well testing system, periodic samples of the well stream are introduced into a vertically disposed fluid analysis chamber after the chamber has been purged of contaminating fluids, it is closed to trap a representative sample of the fluids produced from the well. The fluids in the stilled chamber then stratify vertically into gases at the top followed by clean crude oil, emulsion and then water and basic sediment.

The emulsion section (if present) may be of the type which easily separates into its component oil and water parts, or it may be a hard emulsion which separates only with the addition of heat, chemicals and time.

In the above referenced oil well testing apparatus, a capacitance probe has been used in a manner so that a single reading gives an average permittivity result over the full vertical height of the fluid analysis chamber. This reading, coupled with other data derived from the fluid analysis chamber instrumentation (absolute pressure, absolute temperature and average density) can be used by the computer software to write three equations in three unknowns which can be solved for the quantities of oil, gas and water in the well stream.

For wells wherein the well stream contains no emulsion, the above method of taking a single average permittivity for the stratified column may yield reasonable results. However, it has been discovered that when an emulsion layer is present, the performance of a single average permittivity reading for the column yields spurious results. To overcome this disadvantage of the standard capacitance probes, a novel way of providing the capacitance reading has been provided by the present invention.

Figure 4:
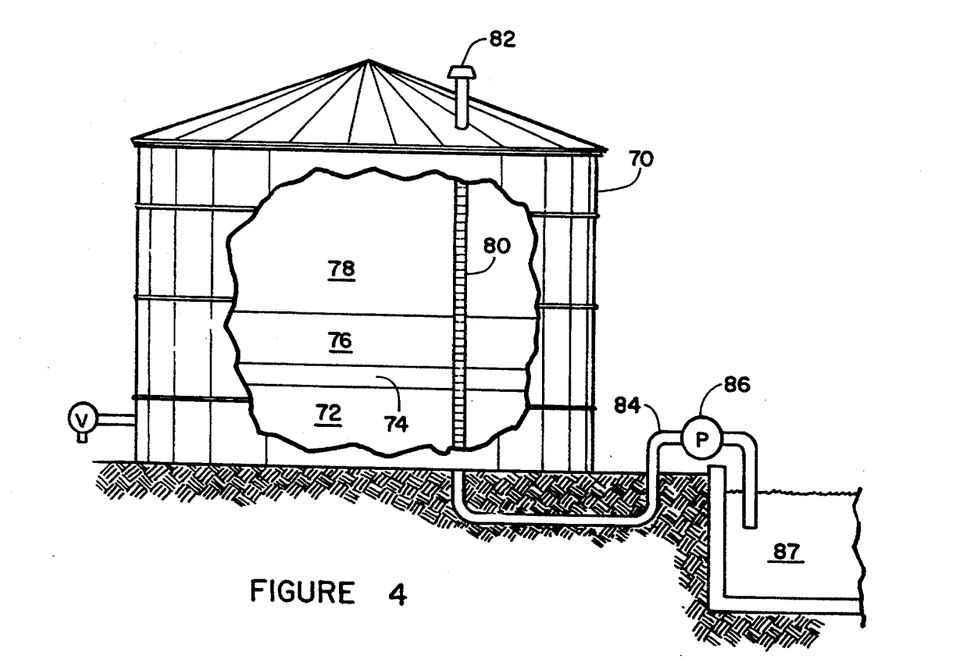
FIG. 4 is a simplified sectional view of another embodiment of the invention as applied to a liquid storage tank.

Referring now to FIG. 4, a suitable storage chamber or tank 70 contains stratified liquids which have different capacitive permittivity values. For example, the bottom layer 72 which may be water fills the tank 70 to approximately 20% of the height of the tank. Next, about 5% of the height above the water later 72 is occupied by an emulsion layer 74. Above this 25% of the tank volume a layer 76 of clean crude oil fills the next 25% of the tank volume, and the top one-half of the tank is hydrocarbon gasses.

Figure 5:
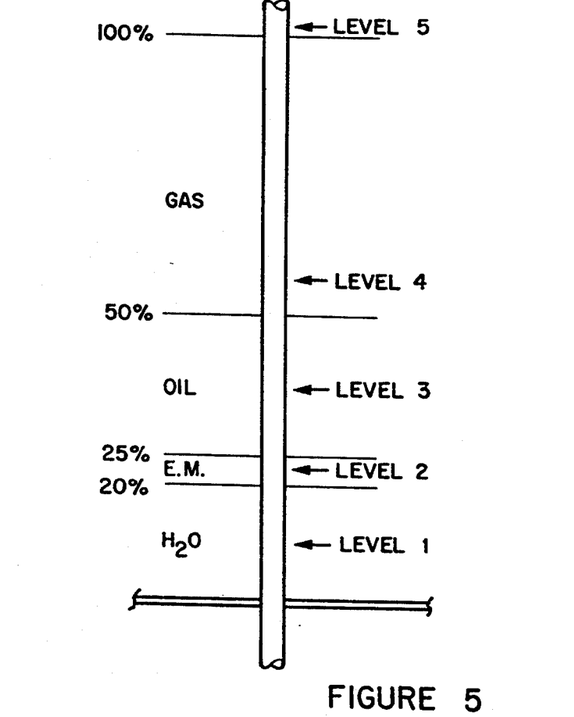
FIG. 5 is a representation of the levels of the various liquids that may be contained in the tank of FIG. 4.

The known permittivity values are approximately as follows:
water —80
emulsion —80 to 5
crude oil —5 to 2
gas —1

In the past a unitary probe has been used to obtain a single average permittivity reading for the total stratified column.

The embodiment of the invention shown in FIG. 4 consists of taking in sequence from the bottom up or the top down a plurality of readings of the permittivity at sequentially higher (or lower) elevations in the sample being measured so that the readings can be individually analyzed and then can be combined in a form so that a graphic analysis of the fluid present at each elevation can be obtained. The data can then be entered in a computer where software can be used to perform specific analysis of the acquired data.

The embodiment of the invention shown in FIG. 4 includes a suitable electrically non-conductive tube 80 which extends vertically through the tank 70 and is suitably vented at its upper end 82. The tube 80 is made of a suitable material such as glass. The lower end of the tube 80 is connected through a suitable conduit 84 to a pump 86 that is connected to a source 88 of electrically conductive liquid such as hot brine.

For ease of illustration, the various electrical connections, capacitance measuring circuitry and computer means and interfaces are not shown but are considered to be part of this arrangement. The brine 88 is introduced at a known or controlled rate into the tube 80. As the level of the conductive liquid 88 rises in the tube 80, the permittivity is measured at a plurality of known levels.

Figure 6:
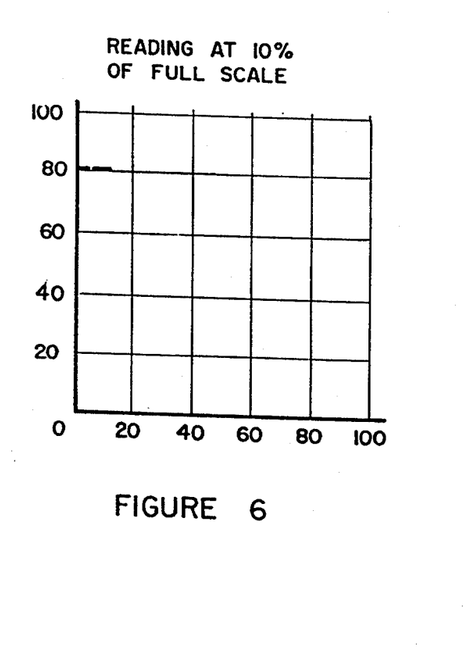
FIGS. 6 to 9 are representations of the capacitance readings taken at various vertical levels within the tank of FIG. 4.
Figure 7:
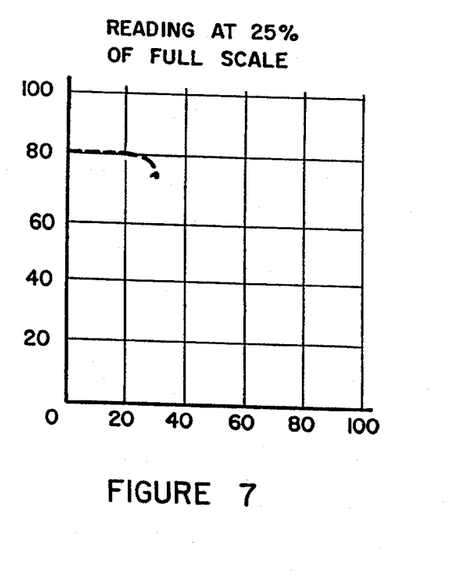
Figure 8:
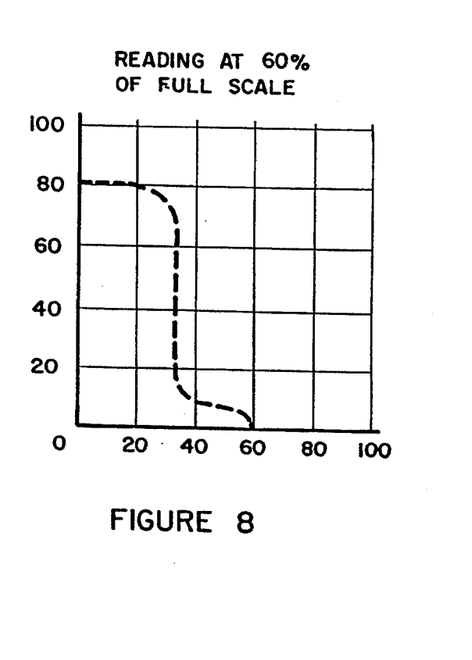
Figure 9:
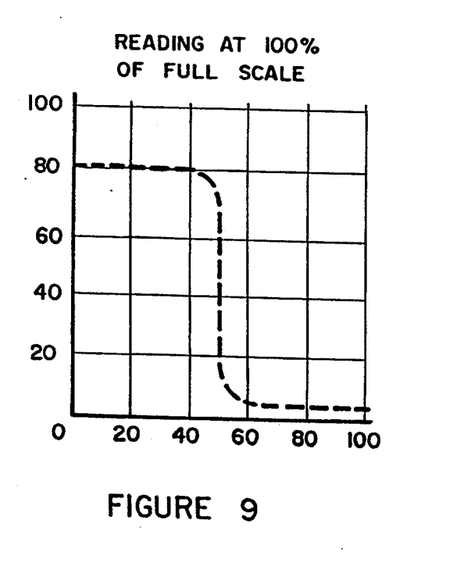

In a tank filled with fluids as described above, a graph of permittivity versus elevation within the tank would appear as in FIG. 6 when the conductive liquid has reached the 20% level of elevation. FIG. 7 shows the graph of permittivity versus elevation at the 25% level. FIG. 8 shows the 40% elevation and FIG. 9 shows the full scale or full elevation.

A primary benefit of the invention relates to the use of a conductive liquid to measure permittivity and the taking of may readings at ascending or descending levels to provide a permittivity elevation profile of the fluids being tested.

The foregoing has illustrated a number of methods of measuring the capacitance of a liquid sample at a number of spaced locations along the vertical axis of a vertical column of a well stream sample and the novel method and capacitance probe arrangements for determining the phase fractions of a liquid contained in a chamber and having various volumetric fractions which have differing permittivities such as those of gas, oil and water and oil-water emulsion of a well stream. The novel method and capacitance probe arrangements makes it theoretically possible to determine accurately such flow fractions when the gas fraction is 0-100% or the oil fraction is 0-100% or the water fraction is 0-100%. The capacitance profile thus provided makes it possible to determine such phase fractions and the oil-emulsion interface on a real time basis and also makes the general mathematical equations for solving for such phase fractions less dependent on other physical measurements that may not be entirely reliable due to changing conditions.

The present disclosure includes that contained in the appended claims as well as that of the foregoing description. Although this invention has been described in its preferred forms. With a certain degree of particularity, it is understood that the present disclosure of the preferred form has been made only by way of example and numerous changes in the details of construction and combination and arrangement of parts and method steps may be resorted to without departing from the spirit and scope of the invention.

What is claimed is:

1. A method for calculating the volumetric phase fractions of a fluid having phase fractions that have different permittivities which comprises:
   introducing a sample of such a fluid in a chamber;
   measuring the capacitance of the sample at a plurality of points along the vertical height of the chamber;
   determining a plurality of other measurements of the contained fluid, said other measurements comprising absolute temperature, absolute pressure and differential pressure generated by known liquid column height, and
   employing such capacitance and other measurements to calculate the volummetric fractions of the contained fluid.

2. The method of claim 1 wherein the measurement of the capacitance of the contained fluid includes disposing an electrically non-conductive tube vertically in the chamber containing the fluid;
   introducing an electrically conductive liquid upwardly into the tube, and
   measuring the capacitance as the conductive fluid rises in the tube.

3. The method of claim 2 wherein the introduction step includes introducing brine into the tube.

4. An arrangement for carrying out the method of claim 1 which includes:
   a tank which contains a liquid having volumetric phase fractions that have different permittivities;
   a vented hollow electrically non-conductive tube which extends vertically through the tank so as to be in contact with the contained liquid;
   a source of an electrically conductive liquid coupled to the bottom of the tube;
   a pump means connected to the source of electrically conductive liquid and adapted to pump such liquid upwardly in the tube in a predetermined controlled manner;
   other measurements means coupled to the tank for determining said plurality of other measurement values related to the contained liquid, and
   calculating means coupled to the capacitance measurement means and to the other measurement means for calculating the volummetric phase fractions of the liquids comprising the contained liquid.

5. The arrangement of claim 4 wherein the liquid contained in the tank is oil having phase fractions of oil, oil-water emulsion, and water with gas interposed over the liquid.

6. The arrangement of claim 5 wherein the tank that is provided with a controllable valve interposed at a lower portion and which may be opened in response to the calculating means to permit water to flow from the tank.

7. The arrangement of claim 1 wherein the sample is held in the chamber for a predetermined time.

8. A method for calculating the volumetric phase fractions of a fluid having phase fractions that have different permittivities which comprises:
   introducing a sample of such a fluid in a chamber;
   measuring the capacitance of the sample at a plurality of points along the vertical height of the chamber by disposing an electrically non-conductive tube vertically in the chamber containing the fluid,
   introducing an electrically conductive liquid upwardly into the tube and
   measuring the capacitance as the conductive fluid rises in the tube;
   determining a plurality of other measurements of the contained fluid said other measurements comprising absolute temperature, absolute pressure and differential pressure generated by known liquid column height, and
   employing such capacitance and other measurements to calculate the volumetric fractions of the contained fluid.

9. The method of claim 8 wherein the introduction step includes introducing brine into the tube.

10. An arrangement for carrying out the method of claim 8 which includes:
    a tank which contains a liquid having volumetric phase fractions that have different permittivities;
    a vented hollow electrically non-conductive tube which extends vertically through the tank so as to be in contact with the contained liquid;
    a source of an electrically conductive liquid coupled to the bottom of the tube;
    a pump means connected to the source of electrically conductive liquid and adapted to pump such liquid upwardly in the tube in a predetermined controlled manner;
    other measurements means coupled to the tank for determining said plurality of other measurement values related to the contained liquid, and
    calculating means coupled to the capacitance measurement means and to the other measurement means for calculating the volumetric phase fractions of the liquids comprising the contained liquid.

11. The arrangement of claim 10 wherein the liquid contained in the tank is oil having phase fractions of oil, oil-water emulsion, and water with gas interposed over the liquid.

12. The arrangement of claim 11 wherein the tank that is provided with a controllable valve interposed at a lower portion and which may be opened in response to the calculating means to permit water to flow from the tank.

* * * * *